(12) United States Patent
Inoue et al.

(10) Patent No.: US 10,233,366 B2
(45) Date of Patent: Mar. 19, 2019

(54) HOT-MELT ADHESIVE AGENT

(71) Applicant: HENKEL AG & CO. KGAA, Duesseldorf (DE)

(72) Inventors: Kentarou Inoue, Osaka (JP); Masahiro Moriguchi, Osaka (JP)

(73) Assignee: HENKEL AG & CO. KGAA, Duesseldorf (DE)

( * ) Notice: Subject to any disclaimer, the term of this patent is extended or adjusted under 35 U.S.C. 154(b) by 0 days.

(21) Appl. No.: 14/921,187

(22) Filed: Oct. 23, 2015

(65) Prior Publication Data

US 2016/0040047 A1 Feb. 11, 2016

Related U.S. Application Data

(63) Continuation of application No. PCT/JP2014/061644, filed on Apr. 18, 2014.

(30) Foreign Application Priority Data

Apr. 23, 2013 (JP) .................................. 2013-090510

(51) Int. Cl.
| | |
|---|---|
| C09J 153/02 | (2006.01) |
| A61L 15/58 | (2006.01) |
| C08L 53/02 | (2006.01) |
| A61L 15/24 | (2006.01) |
| C08K 5/00 | (2006.01) |

(52) U.S. Cl.
CPC ............ C09J 153/02 (2013.01); A61L 15/24 (2013.01); A61L 15/58 (2013.01); A61L 15/585 (2013.01); C08L 53/02 (2013.01); C08K 5/0016 (2013.01); C08L 2205/02 (2013.01)

(58) Field of Classification Search
CPC .................................. C08L 53/02; C09J 153/02
See application file for complete search history.

(56) References Cited

U.S. PATENT DOCUMENTS

| | | | |
|---|---|---|---|
| 5,948,527 A | 9/1999 | Gerard et al. | |
| 2008/0070053 A1 | 3/2008 | Schmierer | |
| 2008/0153971 A1 | 6/2008 | Salazar | |
| 2011/0263782 A1 | 10/2011 | Dubois | |
| 2013/0030096 A1 | 1/2013 | Lietzau | |
| 2016/0009966 A1 | 1/2016 | Inoue et al. | |
| 2016/0040047 A1 | 2/2016 | Inoue et al. | |

FOREIGN PATENT DOCUMENTS

| | | | |
|---|---|---|---|
| CN | 101331203 A | 12/2008 | |
| CN | 101547988 A | 9/2009 | |
| CN | 102264854 A | 11/2011 | |
| EP | 1564273 A1 | 8/2005 | |
| EP | 1564275 A1 | 8/2005 | |
| JP | 6210163 A | 1/1987 | |
| JP | 02232049 A | 9/1990 | |
| JP | 5311138 A | * 11/1993 | |
| JP | 5311138 A | 11/1993 | |
| JP | 05331355 A | 12/1993 | |
| JP | 9-291265 A | 11/1997 | |
| JP | 10-130349 A | 5/1998 | |
| JP | 2000282006 A | 10/2000 | |
| JP | 2000309767 A | 11/2000 | |
| JP | 2004137297 A | 5/2004 | |
| JP | 2004238548 A | 8/2004 | |
| JP | 20068947 A | 1/2006 | |
| JP | 2007530714 A | 11/2007 | |
| JP | 2009511713 A | 3/2009 | |
| JP | 2010506005 A | 2/2010 | |
| JP | 2012021078 A | 2/2010 | |
| JP | 2010536957 A | 12/2010 | |
| JP | WO2014017380 A1 | 7/2016 | |
| WO | 9928405 A1 | 6/1999 | |
| WO | 03027182 A1 | 4/2003 | |

* cited by examiner

*Primary Examiner* — Peter D. Mulcahy

(74) *Attorney, Agent, or Firm* — Sun Hee Lehmann

(57) ABSTRACT

The present invention provides a hot-melt adhesive agent which is capable of applying at low temperature, and has an excellent adhesiveness to a polyolefin substrate, and a disposable product obtained by employing the hot-melt adhesive agent. A hot-melt adhesive agent comprising a thermoplastic block copolymer (A) which is a copolymer of vinyl class aromatic hydrocarbons and conjugated diene compounds, wherein
  the thermoplastic block copolymer (A) comprises the following component (A1) and component (A2):
  (A1) a radial type styrene block copolymer having a styrene content of 35 to 45% by weight and a diblock content of 50 to 90% by weight, and having a viscosity at 25° C. as a 25% (by weight) toluene solution of not more than 250 mPa·s; and
  (A2) a styrene block copolymer having a styrene content of less than 30% by weight, and having a viscosity at 25° C. as a 25% (by weight) toluene solution of more than 250 mPa·s.

8 Claims, No Drawings

HOT-MELT ADHESIVE AGENT

TECHNICAL FIELD OF THE INVENTION

The present invention relates to a hot-melt adhesive agent, and more particularly to a hot-melt adhesive agent used in the field of disposable products typified by a paper diaper and a napkin.

BACKGROUND OF THE INVENTION

An adhesive agent containing a thermoplastic block copolymer as a main component has been used in disposable products typified by a paper diaper and a napkin and, particularly, a hot-melt adhesive agent based on a styrene class block copolymer has widely been used. For example, a paper diaper is produced by bonding a polyethylene film with other members (for example, a nonwoven fabric, an elastic material such as a natural rubber, a water-absorbing paper, etc.) using a hot-melt adhesive agent. The hot-melt adhesive agent can be applied to various members using various methods and, even when using any method, the hot-melt adhesive agent is melted by heating so as to obtain an appropriate viscosity, and then the molten adhesive agent is applied to various constituent members in a dot, linear, stripe, spiral or sheet form.

It is now required for the paper diaper to improve drapeness thereof, and a study has been made in improving flexibility and drapeness of the paper diaper by more thinning a polyethylene film or the above-mentioned various members such as a nonwoven fabric. Thinning of various members significantly reduces material costs. However, thinning of the polyethylene film may cause a problem that heat resistance deteriorates and application of a high-temperature (not lower than 150° C.) hot-melt adhesive agent leads to melting of the polyethylene film or formation of wrinkles of the polyethylene film. Therefore, adhesive agent manufacturers have made a progress on the development of a low-temperature-applicable hot-melt adhesive agent which is capable of applying at low temperature (not higher than 140° C.).

Taking workability and environmental aspect in the case of application of the hot-melt adhesive agent into account, manufacturers producing a paper diaper and a sanitary good strongly desire lowering of the viscosity of the hot-melt adhesive agent. The hot-melt adhesive agent commonly comprises a base polymer and a plasticizer, and a study has been made in lowering the viscosity of the hot-melt adhesive agent by a method in which the amount of the base polymer is decreased to thereby increase the amount of the plasticizer. However, the production of a paper diaper using a low viscosity hot-melt adhesive agent produced using such method may cause a problem that the balance between an adhesiveness to a polyethylene film which composes members of the paper diaper and a retention force (cohesive force) is deteriorated, and the softening point is excessively lowered.

There is also a paper diaper including a rubber thread incorporated thereinto. In the case of incorporating the rubber thread into the paper diaper, the drawn rubber thread is bonded to a paper diaper unit. A hot-melt adhesive agent is usually used as an adhesive agent. The paper diaper unit commonly has no elasticity. Therefore, the paper diaper including the rubber thread bonded thereto is folded by a shrinkage force of the rubber thread when the rubber thread bonded to the paper diaper shrinks. As a result, expansion and shrinkage forces of the rubber thread are applied to the paper diaper unit, and thus enabling the paper diaper to fit the body.

However, if the hot-melt adhesive agent used in bonding of the rubber thread has insufficient creep resistance, it becomes impossible for the hot-melt adhesive agent to hold the rubber thread, which is inclined to shrink, at the position where the rubber thread was bonded to the paper diaper unit. That is, only the rubber thread shrinks without accompanying the paper diaper unit. In that case, even if the rubber thread shrinks, paper diaper unit is not folded and thus expansion and shrinkage forces of the rubber thread are not applied to the paper diaper unit. Therefore, the paper diaper fails to fit the body. In order to solve such inconvenience, the hot-melt adhesive agent is required to have excellent creep resistance together with excellent adhesiveness.

Patent Literatures 1 to 4 disclose hot-melt adhesive agents based on a styrene class block copolymer.

Patent Literature 1 and Patent Literature 2 mention hot-melt adhesive agents including a radial type styrene block copolymer (claim 1 of each patent literature). However, the hot-melt adhesive agents of these patent literatures are unsuitable for application at low temperature since they include a high-viscosity radial type styrene block copolymer, and have neither sufficient tack nor adhesiveness because of a low diblock content of the radial type styrene block copolymer.

Patent Literature 3 discloses a hot-melt adhesive agent including a styrene-butadiene-styrene block copolymer having high styrene content. The hot-melt adhesive agent of Patent Literature 3 is insufficient in any one of application at low temperature, creep resistance and adhesiveness to a polyolefin substrate, as shown in paragraph [0068] of Table 1 and paragraph [0072] of Table 2. Therefore, taking producibility of a paper diaper into account, it is impossible to say that the hot-melt adhesive agent of Patent Literature 3 completely meets high requirements of product manufacturers.

Patent Literature 4 discloses a hot-melt adhesive agent including an ultra-branched styrene type block copolymer (see [claims]). As mentioned in paragraphs [0048] and [0085] to [0088], a viscosity of the adhesive agent including an ultra-branched styrene type block copolymer (Soloprene 9618) is measured at 163° C. Therefore, the hot-melt adhesive agent of Patent Literature 4 does not also take application at low temperature of not higher than 140° C. into account. Reduction in the content of the ultra-branched type styrene type block copolymer enables application of a hot-melt adhesive agent at low temperature, but causes deterioration of the adhesiveness to the polyolefin substrate.

Patent Literature 1: JP 5-311138 A
Patent Literature 2: JP 2006-8947 A
Patent Literature 3: JP 2010-506005 W
Patent Literature 4: JP 2010-536957 W

SUMMARY OF THE INVENTION

An object of the present invention is to provide a hot-melt adhesive agent which is capable of applying at low temperature, and has an excellent adhesiveness to a polyolefin substrate, and a disposable product obtained by employing the hot-melt adhesive agent.

The present invention provides a hot-melt adhesive agent including a thermoplastic block copolymer (A) which is a copolymer of vinyl class aromatic hydrocarbons and conjugated diene compounds, wherein the thermoplastic block copolymer (A) includes the following component (A1) and component (A2):

(A1) a radial type styrene block copolymer having a styrene content of 35 to 45% by weight and a diblock content of 50 to 90% by weight, and having a viscosity at 25° C. as 25% (by weight) toluene solution of not more than 250 mPa·s; and (A2) a styrene block copolymer having a styrene content of less than 30% by weight, and having a viscosity at 25° C. as 25% (by weight) toluene solution of more than 250 mPa·s.

The hot-melt adhesive agent of the present invention includes, in an embodiment, a styrene block copolymer of three branched type as the radial type styrene block copolymer (A1).

The hot-melt adhesive agent of the present invention includes, in an embodiment, a styrene-isoprene block copolymer as the thermoplastic block copolymer (A2).

The hot-melt adhesive agent of the present invention further includes, in an embodiment, a tackifier resin (B), the tackifier resin (B) including an α-methylstyrene resin.

The present invention also provides a disposable product obtained by applying any one of the above hot-melt adhesive agents.

The hot-melt adhesive agent of the present invention is capable of applying at low temperature because of low melt viscosity, and is excellent in adhesiveness to a polyolefin substrate and is also excellent in creep resistance.

The disposable product of the present invention has excellent in fitting property to the body since expansion and shrinkage forces of the rubber thread are effectively applied to a main unit of a product and are maintained when the rubber thread is incorporated into the disposable product.

DETAILED DESCRIPTION OF THE INVENTION

In the present invention, the "thermoplastic block copolymer (A)" is a copolymer obtained by block copolymerization of vinyl class aromatic hydrocarbons with conjugated diene compounds, and is usually a resin composition including those which include a vinyl class aromatic hydrocarbon block and a conjugated diene compound block.

As used herein, the "vinyl class aromatic hydrocarbon" means an aromatic hydrocarbon compound having a vinyl group, and specific examples thereof include styrene, o-methylstyrene, p-methylstyrene, p-tert-butylstyrene, 1,3-dimethylstyrene, α-methylstyrene, vinylnaphthalene, vinylanthracene, and the like. Particularly, styrene is preferable. These vinyl class aromatic hydrocarbons can be used alone or in combination.

The "conjugated diene compound" means a diolefin compound having at least a pair of conjugated double bonds. Specific examples of the "conjugated diene compound" include 1,3-butadiene, 2-methyl-1,3-butadiene (or isoprene), 2,3-dimethyl-1,3-butadiene, 1,3-pentadiene, and 1,3-hexadiene. Particularly, 1,3-butadiene and 2-methyl-1,3-butadiene are preferable. These conjugated diene compounds can be used alone or in combination.

The thermoplastic block copolymer (A) according to the present invention may be either an unhydrogenated product or a hydrogenated product.

Specific examples of the "unhydrogenated product of the thermoplastic block copolymer (A)" include those in which blocks based on the conjugated diene compound are not hydrogenated. Specific examples of the "hydrogenated product of the thermoplastic block copolymer (A)" include block copolymers in which blocks based on the conjugated diene compound are entirely or partially hydrogenated.

A proportion that the "hydrogenated product of the thermoplastic block copolymer (A)" is hydrogenated can be indicated by a "hydrogenation ratio". The "hydrogenation ratio" of the "hydrogenated product of the thermoplastic block copolymer (A)" refers to a proportion of double bonds converted into saturated hydrocarbon bonds by hydrogenation on the basis of all aliphatic double bonds included in the blocks based on the conjugated diene compound. The "hydrogenation ratio" can be measured by an infrared spectrophotometer, a nuclear magnetic resonance spectrometer, and the like.

Specific examples of the "unhydrogenated product of the thermoplastic block copolymer (A)" include a styrene-isoprene block copolymer (also referred to as "SIS") and a styrene-butadiene block copolymer (also referred to as "SBS"). Specific examples of the "hydrogenated product of the thermoplastic block copolymer (A)" include a hydrogenated styrene-isoprene block copolymer (also referred to as "SEPS") and a hydrogenated styrene-butadiene block copolymer (also referred to as "SEBS").

The hot-melt adhesive agent of the present invention includes, as the thermoplastic block copolymer (A), a radial type styrene block copolymer (A1) and a styrene block copolymer (A2).

The content of (A1) is 40 to 80 parts by weight, and preferably 50 to 70 parts by weight, based on 100 parts by weight of the total weight of (A). The content of (A1) within the above range may enable further improvement in applicability at low temperature, creep resistance and adhesiveness to a polyolefin substrate, and thus the hot-melt adhesive agent becomes suitable for use in disposable products.

In the present description, the radial type styrene block copolymer is a branched styrene block copolymer having a structure in which a plurality of linear type styrene block copolymers radially project from a coupling agent as the center. The linear type styrene block copolymer is a linear copolymer in which blocks of styrene are bonded with blocks of conjugated diene.

Specific structure of the radial type styrene block copolymer is shown below.

[Chemical Formula 1]

$$(S-E)_n Y \qquad (1)$$

In the formula, n is an integer of not less than 2, S is a styrene block, E is a conjugated diene compound block, and Y is a coupling agent. n is preferably 3 or 4, and n is particularly preferably 3. The polymer in which n is 3 is referred to as a three branched type, while the copolymer in which n is 4 is referred to as a four branched type. When n is 3, the obtained hot-melt adhesive agent exhibits low melt viscosity and high retention force (cohesive force). The conjugated diene compound is preferably butadiene or isoprene.

The radial type styrene block copolymer (A1) in the present invention is a resin composition, and includes a styrene-conjugated diene block copolymer represented by the formula:

[Chemical Formula 2]

$$S-E \qquad (2)$$

wherein S and E have the same meanings as defined above, in a given proportion. The styrene-conjugated diene block copolymer of the formula (2) may be sometimes called "diblock".

The coupling agent is a polyfunctional compound which radially bonds a linear type styrene block copolymer. There is no particular limitation on types of the coupling agent.

Examples of the coupling agent include a silane compound such as halogenated silane or alkoxysilane, a tin compound such as halogenated tin, an epoxy compound such as a polycarboxylate ester or epoxydized soybean oil, an acrylic ester such as pentaerythritol tetraacrylate, a divinyl compound such as epoxysilane or divinylbenzene, and the like. Specific examples thereof include trichlorosilane, tribromosilane, tetrachlorosilane, tetrabromosilane, methyltrimethoxysilane, ethyltrimethoxysilane, vinyltrimethoxysilane, vinyltriethoxysilane, tetramethoxysilane, tetraethoxysilane, tetrachlorotin, diethyl adipate, and the like In the present invention, the radial type styrene block copolymer (A1) has a styrene content of 35 to 45% by weight, a diblock content of 50 to 90% by weight, and has a viscosity at 25° C. as a 25% (by weight) toluene solution of not more than 250 mPa·s.

The "styrene content" refers to a proportion of a styrene block included in (A1). The styrene content is 35 to 45% by weight, and more preferably 35 to 40% by weight.

The styrene content of (A1) is within the above range, whereby, the hot-melt adhesive agent of the present invention becomes excellent in balance between retention force (cohesive force), tack and adhesiveness.

The "diblock content" refers to a proportion of a styrene-conjugated diene compound block copolymer of the formula (2) included in (A1). The diblock content is 50 to 90% by weight, and more preferably 55 to 85% by weight.

The diblock content of (A1) is within the above range, whereby the hot-melt adhesive agent of the present invention becomes excellent in tack and adhesiveness. The diblock content of (A1) of less than 50% by weight may sometimes cause deterioration of either adhesiveness or tack of the obtained hot-melt adhesive agent because of excessive content of a branched structure component represented by the formula (1). The diblock content of (A1) of more than 90% by weight may make it difficult to enhance the adhesiveness of the hot-melt adhesive agent even in the case of having a radial structure.

The "viscosity at 25° C. as a 25% (by weight) toluene solution" refers to a viscosity at 25° C. as a solution having a concentration of 25% by weight using toluene as a solvent, and can be measured using various viscometers, for example, a Brookfield BM-type viscometer (spindle No. 27).

The viscosity at 25° C. as a 25% (by weight) toluene solution" of (A1) is not more than 250 mPa·s, and ranges from 100 to 250 mPa·s. Particularly, the viscosity is more preferably 130 to 200 mPa·s.

In the hot-melt adhesive agent of the present invention, the viscosity at 25° C. as a 25% (by weight) toluene solution" of (A1) within the above range may cause significant decrease in melt viscosity, leading to easy application at low temperature.

HJ10, HJ12, HJ13, and HJ15 are commercially available from Asahi Kasei Chemicals Corporation as the radial type styrene block copolymer (A1).

In the present invention, the thermoplastic block copolymer (A) includes a styrene block copolymer (A2). The content of (A2) is 10 to 60 parts by weight, preferably 25 to 50 parts by weight, and more preferably 30 to 45 parts by weight, based on 100 parts by weight of the total weight of (A). The content of (A2) within the above range may enable further improvement in adhesiveness to a polyolefin substrate, creep resistance and applicability at low temperature, and thus the hot-melt adhesive agent becomes suitable for use in disposable products.

The styrene block copolymer (A2) is a polymer which has a styrene content of less than 30% by weight, and has a viscosity at 25° C. as a 25% (by weight) toluene solution of more than 250 mPa·s. Therefore, (A2) is clearly distinguished from (A1).

The styrene block copolymer (A2) preferably has a styrene content of 10 to 28% by weight, and more preferably 15 to 26% by weight. The styrene block copolymer (A2) preferably has a viscosity at 25° C. as a 25% (by weight) toluene solution of 290 to 500 mPa·s, and more preferably 310 to 400 mPa·s.

Inclusion of (A2) enables the hot-melt adhesive agent of the present invention to become excellent in elasticity maintenance (creep resistance) of a rubber thread and adhesiveness.

(A2) preferably includes a styrene-isoprene block copolymer. Inclusion of the styrene-isoprene block copolymer enables further improvement in creep resistance while maintaining adhesiveness to a polyolefin substrate, and thus the hot-melt adhesive agent becomes suitable for use in paper diapers.

It is possible to use, as the styrene block copolymer (A2), commercially available products. Examples thereof include Quintac 3460 (trade name) and Quintac 3270 (trade name) manufactured by Zeon Corporation.

The thermoplastic block copolymer (A) of the present invention may include other styrene block copolymers (A3) which do not correspond to (A1) or (A2).

It is possible to use, as other styrene block copolymers (A3), commercially available products. Examples of commercially available products include Asaprene T439 (trade name), Asaprene T436 (trade name) and Asaprene T432 (trade name) manufactured by Asahi Kasei Chemicals Corporation; TR2500 (trade name) manufactured by JSR Corporation; Sol T6414 (trade name) and Sol T166 (trade name) manufactured by Enichem Ltd.; Taipol 4202 (trade name) manufactured by TSRC Corporation; and Soloprene 9618 (trade name) manufactured by Dynasol Inc.

The hot-melt adhesive agent of the present invention preferably includes a tackifier resin (B) and a plasticizer (C). The tackifier resin (B) is usually used in the hot-melt adhesive agent and is not particularly limited as long as the objective hot-melt adhesive agent of the present invention is obtainable.

Examples of such tackifier resin (B) include a natural rosin, a modified rosin, a hydrogenated rosin, a glycerol ester of a natural rosin, a glycerol ester of a modified rosin, a pentaerythritol ester of a natural rosin, a pentaerythritol ester of a modified rosin, a pentaerythritol ester of a hydrogenated rosin, a copolymer of a natural terpene, a three dimensional polymer of a natural terpene, hydrogenated derivatives of a copolymer of a hydrogenated terpene, a polyterpene resin, hydrogenated derivatives of a phenol class modified terpene resin, an aliphatic petroleum hydrocarbon resin, hydrogenated derivatives of an aliphatic petroleum hydrocarbon resin, an aromatic petroleum hydrocarbon resin, hydrogenated derivatives of an aromatic petroleum hydrocarbon resin, a cyclic aliphatic petroleum hydrocarbon resin, and hydrogenated derivatives of a cyclic aliphatic petroleum hydrocarbon resin. These tackifier resins can be used alone or in combination. It is also possible to use, as the tackifier resin, a liquid type tackifier resin as long as it has a colorless to pale yellow color tone and has substantially no odor, and also has satisfactory thermal stability.

It is possible to use, as the tackifier resin (B), commercially available products. Examples of such commercially available products include ECR179EX (trade name) manufactured by Tonex Co., Ltd.; Maruka Clear H (trade name) manufactured by Maruzen Petrochemical CO, LTD.; Alcon M100 (trade name) manufactured by Arakawa Chemical Industries, Ltd.; I-MARV S100 (trade name) manufactured by IDEMITSU KOSAN CO., LTD.; Clearon K100 (trade name), Clearon K4090 (trade name) and Clearon K4100 manufactured by YASUHARA CHEMICAL CO., LTD.; ECR179EX (trade name) and ECR231C (trade name) manufactured by Tonex Co., Ltd.; Regalite C6100L (trade name) and Regalite C8010 (trade name) manufactured by Eastman Chemical Company; and FTR2140 (trade name) manufactured by Mitsui Chemicals, Inc. Examples of the unhydrogenated tackifier resin include Quinton DX390N (trade name) and Quinton DX395 (trade name) manufactured by Zeon Corporation. These commercially available tackifier resins can be used alone or in combination.

The tackifier resin (B) preferably includes an aromatic resin which is referred to as an end-block resin. The end-block resin is a polymer of an aromatic monomer having a polymerizable unsaturated group. Typical examples of the aromatic monomer include styrenic monomers such as styrene, α-methylstyrene, vinyltoluene, methoxystyrene, tertiarybutylstyrene and chlorostyrene, and indene monomers such as indene and methylindene.

Inclusion of the end-block resin in the hot-melt adhesive agent of the present invention enables an improvement in cohesive force, leading to enhanced adhesiveness and improved creep resistance.

In the present invention, the end-block resin is preferably an α-methylstyrene resin. Examples of commercially available products of the α-methylstyrene resin include KRISTALEX series and PLASTOLYN series manufactured by Eastman Chemical Company.

The plasticizer (C) is blended for the purpose of decreasing melt viscosity of the hot-melt adhesive agent, imparting flexibility to the hot-melt adhesive agent, and improving wettability of the hot-melt adhesive agent to an adherend. There is no particular limitation as long as the plasticizer is compatible with the block copolymer and the objective hot-melt adhesive agent of the present invention is obtainable. Examples of the plasticizer (C) include paraffin oil, naphthene oil and aromatic oil. Colorless and odorless naphthene oil is particularly preferable.

It is possible to use, as the plasticizer (C), commercially available products. Examples thereof include White Oil Broom 350 (trade name) manufactured by Kukdong Oil & Chemicals Co., Ltd.; Diana Fresia S32 (trade name), Diana Process Oil PW-90 (trade name) and DN Oil KP-68 (trade name) manufactured by IDEMITSU KOSAN CO., LTD.; Enerper M1930 (trade name) manufactured by BP Chemicals, Inc.; Kaydol (trade name) manufactured by Crompton Corporation; Primol352 (trade name) manufactured by ESSO Corp.; Process Oil NS100 manufactured by IDEMITSU KOSAN CO., LTD.; and KN4010 (trade name) manufactured by PetroChina Company Limited. These plasticizers (C) can be used alone or in combination.

In the hot-melt adhesive agent of the present invention, the content of (A) is 3 to 60 parts by weight, preferably 10 to 45 parts by weight, and more preferably 20 to 35 parts by weight, based on 100 parts by weight of the total weight of (A) to (C). The content of (A) within the above range may enable the hot-melt adhesive agent to be excellent in adhesiveness to a polyolefin substrate and creep resistance, and to be capable of applying at low temperature.

The content of (B) is 30 to 90 parts by weight, preferably 45 to 75 parts by weight, and more preferably 50 to 70 parts by weight, based on 100 parts by weight of the total weight of (A) to (C). Among (B), the end-block resin is used in the amount of not more than 40 parts by weight, and preferably 1 to 10 parts by weight, if necessary. The content of (C) is commonly 5 to 30 parts by weight, and preferably 10 to 20 parts by weight, based on 100 parts by weight of the total weight of (A) to (C).

If necessary, the hot-melt adhesive agent according to the present invention may further contain various additives. Examples of such various additives include a stabilizer and a fine particle filler.

The "stabilizer" is blended so as to prevent decrease in molecular weight, occurrence of gelation, coloration, odor and the like of the hot-melt adhesive agent due to heat, thereby improving stability of the hot-melt adhesive agent, and there is no particular limitation as long as the objective hot-melt adhesive agent of the present invention is obtainable. Examples of the "stabilizer" include an antioxidant and an ultraviolet absorber.

The "ultraviolet absorber" is used so as to improve light resistance of the hot-melt adhesive agent. The "antioxidant" is used so as to prevent oxidative degradation of the hot-melt adhesive agent. There is no particular limitation on the antioxidant and the ultraviolet absorber, as long as they are commonly used in disposable products and the below-mentioned objective disposable products are obtainable.

Examples of the antioxidant include phenol antioxidants, sulfur antioxidants and phosphorous antioxidants. Examples of the ultraviolet absorber include benzotriazole ultraviolet absorbers and benzophenone ultraviolet absorbers. It is also possible to add lactone stabilizers. These additives can be used alone or in combination.

It is possible to use, as the stabilizer, commercially available products. Examples thereof include SUMILIZER GM (trade name), SUMILIZER TPD (trade name) and SUMILIZER TPS (trade name) manufactured by Sumitomo Chemical Co. Ltd.; IRGANOX 1010 (trade name), IRGANOX HP2225FF (trade name), IRGAFOS 168 (trade name) and IRGANOX 1520 (trade name) manufactured by Ciba Specialty Chemicals Inc.; and JF77 (trade name) manufactured by Johoku Chemical Co., Ltd. These stabilizers can be used alone or in combination.

The hot-melt adhesive agent of the present invention is produced by blending the above components in a given proportion, optionally blending various additives, and melting the mixture with heating, followed by mixing. Specifically, the hot-melt adhesive agent is produced by charging the above components in a melt-mixing vessel equipped with a stirrer, followed by mixing with heating.

The obtained hot-melt adhesive agent preferably has a melt viscosity at 160° C. of not more than 3,000 mPa·s and a melt viscosity at 140° C. of not more than 7,000 mPa·s. The "melt viscosity" refers to a viscosity in molten state of the hot-melt adhesive agent and is measured by a Brookfield RVT-type viscometer (spindle No. 27). The hot-melt adhesive agent according to the present invention is capable of applying at low temperature (not higher than 140° C.) because of having a viscosity at 140° C. of not higher than 7,000 mPa·s.

The hot-melt adhesive agent according to the present invention preferably has a maintenance rate of not less than 80%, and more preferably more than 90%, measured by the method for evaluation of elasticity maintenance (creep resistance) of the rubber thread mentioned in Examples. Elasticity maintenance of not less than 80% enables that elasticity of the rubber thread incorporated into disposable products such as a paper diaper is maintained, and thus the hot-melt adhesive agent is suitable for use in disposable products.

The hot-melt adhesive agent according to the present invention preferably has a peel strength (20° C.) of not less than 1,500 gf/inch (14.7 N/2.54 cm), and more preferably 2,000 gf/inch (19.6 N/2.54 cm), measured by the method for evaluation of peel strength mentioned in Examples. Peel strength of not less than 1,500 gf/inch (14.7 N/2.54 cm) may enable an improvement in adhesiveness to a polyolefin substrate to be incorporated into a disposable product, and thus the hot-melt adhesive agent becomes an adhesive agent suitable for assembling a disposable product by laying the polyolefin substrate.

The hot-melt adhesive agent according to the present invention preferably has loop tack of not less than 1,500 gf/inch (14.7 N/2.54 cm), and particularly preferably not less than 2,000 gf/inch (19.6 N/2.54 cm), measured by the method for evaluation of loop tack mentioned in Examples. Peel strength of 1,500 gf/inch (14.7 N/2.54 cm) may enable the production of a hot-melt adhesive agent which is excellent in initial tack and is suitable as an adhesive agent for disposable products.

The hot-melt adhesive agent according to the present invention is widely used in paper processing, bookbinding, disposable products, and the like, and is mainly used in disposable products. There is no particular limitation on "disposable products" as long as they are so-called sanitary materials. Specific examples thereof include a paper diaper, a sanitary napkin, a pet sheet, a hospital gown, a surgical white garment, and the like.

The hot-melt adhesive agent of the present invention is particularly preferably used for the purpose of bonding a drawn rubber thread to a main unit of a product in the case of producing the above disposable product including a rubber thread incorporated therein.

The present invention provides, in another aspect, a disposable product obtained by non-contact coating of the above hot-melt adhesive agent at low temperature (not higher than 140° C.). The disposable product is constituted by bonding at least one member selected from the group consisting of a woven fabric, a nonwoven fabric, a rubber, a resin and papers with a polyolefin film using the hot-melt adhesive agent according to the present invention. The polyolefin film is preferably a polyethylene film for the reason of durability, costs and the like.

In the production line for the disposable product, the hot-melt adhesive agent is commonly applied to at least one of various members (for example, nonwoven fabric, etc.) of the disposable product, and a polyolefin film, and then the film is contact-bonded with the members to produce a disposable product. In the case of applying, the hot-melt adhesive agent may be discharged from various ejectors. In the present invention, the "non-contact coating" method refers to a coating method in which a discharger is not brought into contact with a member or a film in the case of applying the hot-melt adhesive agent. Specific examples of the non-contact coating method include a spiral coating method capable of coating in a spiral form, an omega coating or control seam coating method capable of coating in a wavy form, a slot spray coating or curtain spray coating method capable of coating in a plane form, a dot coating method capable of coating in a dot form, and the like.

EXAMPLES

The present invention will be described for the purpose of describing the present invention in more detail and specific manner by way of Examples and Comparative Examples. These are exemplary of the present invention and are not to be considered as limiting.

In Examples, unless otherwise specified, parts by weight and percentages by weight are based on the places where a solvent is not taken into account.

Components used in the present Examples are shown below.

(A) Thermoplastic Block Copolymer
<(A1) Radial Type Styrene Block Copolymer>
(A1-1) Styrene-butadiene block copolymer of three branched type (styrene content of 39% by weight, diblock content of 80% by weight, viscosity at 25° C. as 25% (by weight) toluene solution of 165 mPa·s, HJ13 (manufactured by Asahi Kasei. Chemicals Corporation))
(A1-2) Styrene-butadiene block copolymer of three branched type (styrene content of 39% by weight, diblock content 80% by weight, viscosity at 25° C. as 25% (by weight) toluene solution of 189 mPa·s, HJ13-2 (manufactured by Asahi Kasei Chemicals Corporation))
(A1-3) styrene-butadiene block copolymer of three branched type (styrene content 38% by weight, diblock content 60% by weight, viscosity at 25° C. as 25% (by weight) toluene solution of 177 mPa·s, HJ10 (manufactured by Asahi Kasei Chemicals Corporation))
<(A2) Styrene Block Copolymer>
(A2-1) Styrene-isoprene block copolymer of three branched type (styrene content of 25% by weight, diblock content of 40% by weight, viscosity at 25° C. as 25% (by weight) toluene solution of 380 mPa·s, Quintac 3460 (manufactured by Zeon Corporation))
(A2-2) Styrene-isoprene block copolymer of linear type (styrene content of 24% by weight, diblock content of 70% by weight, viscosity at 25° C. as 25% (by weight) toluene solution of 320 mPa·s, Quintac 3270 (manufactured by Zeon Corporation))
<(A3) Other Styrene Block Copolymers>
(A3-1) Styrene-butadiene block copolymer of linear type (styrene content of 43% by weight, diblock content of 60% by weight, viscosity at 25° C. as 25% (by weight) toluene solution of 170 mPa·s, Asaprene T439 (manufactured by Asahi Kasei Chemicals Corporation))
(A3-2) Styrene-butadiene block copolymer of linear type (styrene content of 40% by weight, diblock content of 0% by weight, viscosity at 25° C. as 25% (by weight) toluene solution of 620 mPa·s, Taipol 4202 (manufactured by TSRC Corporation))
(A3-3) Styrene-butadiene block copolymer of three branched type (styrene content of 35% by weight, diblock content of 40% by weight, viscosity at 25° C. as 25% (by weight) toluene solution of 490 mPa·s, JSR TR2500 (manufactured by JSR Corporation))
(A3-4) Styrene-butadiene block copolymer of 14.2 branched type (styrene content of 30% by weight, diblock content of 50% by weight, viscosity at 25° C. as 25% (by weight) toluene solution of 600 mPa·s, Soloprene 9618 (manufactured by Dynasol Inc.)) (A3-5) Styrene-butadiene block copolymer of four branched type (styrene content of 40% by weight, diblock content of 20% by weight, viscosity at 25° C. as 25% (by weight) toluene solution of 400 mPa·s, SOIT6414 (manufactured by Enichem Ltd.))
(B) Tackifier Resin
(B1) Hydrogenated tackifier resin (Alcon M100 (manufactured by Arakawa Chemical Industries, Ltd.))
(B2) Hydrogenated tackifier resin (ECR179EX (manufactured by Exxon Mobil Corporation))

(B3) Hydrogenated tackifier resin (I-MARV S100N (manufactured by IDEMITSU KOSAN CO., LTD.))
(B4) Unhydrogenated tackifier resin (Quinton DX390N (manufactured by Zeon Corporation))
(B5) Liquid tackifier resin (Maruka Clear H (manufactured by Maruzen Petrochemical CO, LTD.))
(B6) End-block tackifier resin (Plastolyn 240 (manufactured by Eastman Chemical Company))
(B7) End-block hydrogenated tackifier resin (Plastolyn 290 (manufactured by Eastman Chemical Company))
  (C) Plasticizer
(C1) Paraffin oil (Diana Fresis S-32 (manufactured by IDEMITSU KOSAN CO., LTD.))
(C2) Naphthene oil (KN4010 (manufactured by PetroChina Company Limited))
(C3) Naphthene oil (Process Oil NS100 (manufactured by IDEMITSU KOSAN CO., LTD.))
(C4) Paraffin oil (Daphne Oil KP68 (manufactured by IDEMITSU KOSAN CO., LTD.))
  (D) Antioxidant
(D1) Phenol antioxidants (SUMILIZER GM (manufactured by Sumitomo Chemical Co., Ltd.))
(D2) Sulfur antioxidants (SUMILIZER TPD (manufactured by Sumitomo Chemical Co., Ltd.))
(D3) Benzotriazole antioxidants (JF77 (manufactured by Johoku Chemical Co., Ltd.))

Preparation of hot-melt adhesive agents of Examples 1 to 5 and Comparative Examples 1 to 8.

The respective components were blended according to the formulations shown in Tables 1 to 3, and then melt-mixed at about 150° C. to prepare hot-melt adhesive agents. In Tables 1 to 3, "St" means a styrene content, "diblock" means a diblock content, and "TV" means a viscosity at 25° C. as a 25% (by weight) toluene solution.

TABLE 1

| | | | Example 1 | Example 2 | Example 3 | Example 4 | Example 5 |
|---|---|---|---|---|---|---|---|
| (A) | (A1-1) | Three branched radial (St: 39%, diblock: 80%, TV: 165 mPa · s) | 16 | | | 15 | |
| | (A1-2) | Three branched radial (St: 39%, diblock: 80%, TV: 189 mPa · s) | | 19 | 16 | | |
| | (A1-3) | Three branched radial (St: 38%, diblock: 60%, TV: 177 mPa · s) | | | | | 16 |
| | (A2-1) | Three branched radial (St: 25%, diblock: 40%, TV: 380 mPa · s) | 5 | 8 | 10 | 10 | |
| | (A2-2) | Linear (St: 24%, diblock: 70%, TV: 320 mPa · s) | 5 | | | | 10 |
| | (A3-1) | Linear (St: 43%, diblock: 60%, TV: 170 mPa · s) | | | | | |
| | (A3-2) | Linear (St: 40%, diblock: 0%, TV: 620 mPa · s) | | | | | |
| | (A3-3) | Three branched radial (St: 35%, diblock: 40%, TV: 490 mPa · s) | | | | | |
| | (A3-4) | 14.2 Branched radial (St: 30%, diblock: 50%, TV: 600 mPa · s) | | | | | |
| | (A3-5) | Four branched radial (St: 40%, diblock: 20%, TV: 400 mPa · s) | | | | | |
| | | Total weight of (A) | 26 | 27 | 26 | 25 | 26 |
| (B) | (B1) | Tackifier resin (hydrogenated) | 25.5 | 24.5 | 37.5 | 46.5 | 25.5 |
| | (B2) | Tackifier resin (hydrogenated) | | | 15 | | |
| | (B3) | Tackifier resin (hydrogenated) | 15 | 15 | | | 15 |
| | (B4) | Tackifier resin (unhydrogenated) | 15 | 15 | | 10 | 15 |
| | (B5) | Tackifier resin (liquid) | | | | | |
| | (B6) | Tackifier resin (End-block resin) | | | 4.5 | | |
| | (B7) | Tackifier resin (End-block resin) | 4.5 | 4.5 | | 4.5 | 4.5 |
| (C) | (C1) | Paraffin oil | 14 | 14 | | 14 | 14 |
| | (C2) | Naphthene oil | | | 17 | | |
| | (C3) | Naphthene oil | | | | | |
| | (C4) | Paraffin oil | | | | | |
| | | Total weight of (A) to (C) | 100 | 100 | 100 | 100 | 100 |
| (D) | (D1) | Antioxidant | 0.2 | 0.2 | 0.2 | 0.2 | 0.2 |
| | (D2) | Antioxidant | 0.3 | 0.3 | 0.3 | 0.3 | 0.3 |
| | (D3) | Antioxidant | 0.2 | 0.2 | 0.2 | 0.2 | 0.2 |

TABLE 2

| | | | Comp. Example 1 | Comp. Example 2 | Comp. Example 3 | Comp. Example 4 | Comp. Example 5 |
|---|---|---|---|---|---|---|---|
| (A) | (A1-1) | Three branched radial (St: 39%, diblock: 80%, TV: 165 mPa · s) | 28 | 12 | 16 | | |
| | (A1-2) | Three branched radial (St: 39%, diblock: 80%, TV: 189 mPa · s) | | | | | |
| | (A1-3) | Three branched radial (St: 38%, diblock: 60%, TV: 177 mPa · s) | | | | | |

TABLE 2-continued

|   |   |   | Comp. Example 1 | Comp. Example 2 | Comp. Example 3 | Comp. Example 4 | Comp. Example 5 |
|---|---|---|---|---|---|---|---|
| (A) | (A2-1) | Three branched radial (St: 25%, diblock: 40%, TV: 380 mPa · s) | | | | | 10 |
|   | (A2-2) | Linear (St: 24%, diblock: 70%, TV: 320 mPa · s) | | | | | |
|   | (A3-1) | Linear (St: 43%, diblock: 60%, TV: 170 mPa · s) | | 15 | | | |
|   | (A3-2) | Linear (St: 40%, diblock: 0%, TV: 620 mPa · s) | | | | | |
|   | (A3-3) | Three branched radial (St: 35%, diblock: 40%, TV: 490 mPa · s) | | | | 30 | 20 |
|   | (A3-4) | 14.2 Branched radial (St: 30%, diblock: 50%, TV: 600 mPa · s) | | | | | |
|   | (A3-5) | Four branched radial (St: 40%, diblock: 20%, TV: 400 mPa · s) | | | 10 | | |
|   |   | Total weight of (A) | 28 | 27 | 26 | 30 | 30 |
| (B) | (B1) | Tackifier resin (hydrogenated) | | 57 | | | |
|   | (B2) | Tackifier resin (hydrogenated) | 57 | | 25.5 | 50 | 50 |
|   | (B3) | Tackifier resin (hydrogenated) | | | 15 | | |
|   | (B4) | Tackifier resin (unhydrogenated) | | | 15 | | |
|   | (B5) | Tackifier resin (liquid) | | | | | |
|   | (B6) | Tackifier resin (End-block resin) | | | | | |
|   | (B7) | Tackifier resin (End-block resin) | | | 4.5 | | |
| (C) | (C1) | Paraffin oil | 15 | 16 | 14 | | |
|   | (C2) | Naphthene oil | | | | | |
|   | (C3) | Naphthene oil | | | | 20 | 20 |
|   | (C4) | Paraffin oil | | | | | |
|   |   | Total weight of (A) to (C) | 100 | 100 | 100 | 100 | 100 |
| (D) | (D1) | Antioxidant | 0.2 | 0.2 | 0.2 | 0.2 | 0.2 |
|   | (D2) | Antioxidant | 0.3 | 0.3 | 0.3 | 0.3 | 0.3 |
|   | (D3) | Antioxidant | 0.2 | 0.2 | 0.2 | 0.2 | 0.2 |

TABLE 3

|   |   |   | Comp. Example 6 | Comp. Example 7 | Comp. Example 8 |
|---|---|---|---|---|---|
| (A) | (A1-1) | Three branched radial (St: 39%, diblock: 80%, TV: 165 mPa · s) | | | |
|   | (A1-2) | Three branched radial (St: 39%, diblock: 80%, TV: 189 mPa · s) | | | |
|   | (A1-3) | Three branched radial (St: 38%, diblock: 60%, TV: 177 mPa · s) | | | |
|   | (A2-1) | Three branched radial (St: 25%, diblock: 40%, TV: 380 mPa · s) | | | |
|   | (A2-2) | Linear (St: 24%, diblock: 70%, TV: 320 mPa · s) | | | |
|   | (A3-1) | Linear (St: 43%, diblock: 60%, TV: 170 mPa · s) | | | |
|   | (A3-2) | Linear (St: 40%, diblock: 0%, TV: 620 mPa · s) | | 18 | 23 |
|   | (A3-3) | Three branched radial (St: 35%, diblock: 40%, TV: 490 mPa · s) | | | |
|   | (A3-4) | 14.2 Branched radial (St: 30%, diblock: 50%, TV: 600 mPa · s) | 18 | | |
|   | (A3-5) | Four branched radial (St: 40%, diblock: 20%, TV: 400 mPa · s) | | | |
|   |   | Total weight of (A) | 18 | 18 | 23 |
| (B) | (B1) | Tackifier resin (hydrogenated) | 54 | 54 | 55 |
|   | (B2) | Tackifier resin (hydrogenated) | | | |
|   | (B3) | Tackifier resin (hydrogenated) | | | |
|   | (B4) | Tackifier resin (unhydrogenated) | | | |
|   | (B5) | Tackifier resin (liquid) | | | |
|   | (B6) | Tackifier resin (End-block resin) | 10 | | |
|   | (B7) | Tackifier resin (End-block resin) | | 10 | 5 |
| (C) | (C1) | Paraffin oil | | | |
|   | (C2) | Naphthene oil | | | |
|   | (C3) | Naphthene oil | | | 17 |
|   | (C4) | Paraffin oil | 18 | 18 | |
|   |   | Total weight of (A) to (C) | 100 | 100 | 100 |
| (D) | (D1) | Antioxidant | 0.2 | 0.2 | 0.2 |
|   | (D2) | Antioxidant | 0.3 | 0.3 | 0.3 |
|   | (D3) | Antioxidant | 0.2 | 0.2 | 0.2 |

With respect to the thus obtained hot-melt adhesive agents of Example and Comparative Examples, a melt viscosity, a peel strength, loop tack, a coating temperature, and an elasticity maintenance ability of a rubber thread were examined. The results are shown in Tables 4 to 6. The above properties were evaluated by the following methods.

[Melt Viscosity]

A hot-melt adhesive agent was melted by heating at 140° C. and 160° C., and then a viscosity in a molten state was measured using a Brookfield RVT type viscometer (spindle No. 27). Evaluation criteria are as follows.

| | |
|---|---|
| A | Viscosity at 140° C. is not more than 6,000 mPa · s |
| B | Viscosity at 140° C. is more than 6,000 mPa · s and not more than 8,000 mPa · s |
| C | Viscosity at 140° C. is more than 8,000 mPa · s |

| | |
|---|---|
| A | Viscosity at 160° C. is not more than 2,500 mPa · s |
| B | Viscosity at 160° C. is more than 2,500 mPa · s and not more than 3,500 mPa · s |
| C | Viscosity at 160° C. is more than 3,500 mPa · s |

[Peel Strength]

A hot-melt adhesive agent was applied to a 50 μm thick PET film in a thickness of 50 μm. The coated PET film was formed into 2.5 cm wide strips to obtain specimens. Each specimen was laid on a 100 μm thick polyethylene film at 20° C., followed by being left to stand at 20° C. for 1 day. Thereafter, peeling was performed at 20° C. at a tension speed of 300 mm/minute and the peel strength was measured.

| | |
|---|---|
| A | Peel strength is more than 2,000 (g/25 mm) |
| B | Peel strength is 1,500 (g/25 mm) to 2,000 (g/25 mm) |
| C | Peel strength is less than 1,500 (g/25 mm) |

[Loop Tack]

A hot-melt adhesive agent was applied to a 50 μm thick PET film in a thickness of 50 μm. The coated PET film was formed into a size measuring 2.5 cm×10 cm to obtain specimens. Each specimen was wound in a loop form so that an adhesive surface (surface to be coated with an adhesive agent) faces outside, and then the loop was brought into contact with a PE sheet at 20° C. at a speed of 300 mm/minute. Then, the specimen was peeled from the PE sheet at a speed of 300 mm/minute to thereby measure the peel strength at the time of peeling, which was regarded as initial loop tack. The specimen was stored at 20° C. for a week and then brought into contact with the PE sheet at 20° C. at a speed of 300 mm/minute. Then, specimen was peeled from the PE sheet at a speed of 300 mm/minute and the peel strength at the time of peeling, which was regarded as loop tack after a week.

| | |
|---|---|
| A | Loop tack is more than 2,000 (g/25 mm) |
| B | Loop tack is 1,500 (g/25 mm) to 2,000 (g/25 mm) |
| C | Loop tack is less than 1,500 (g/25 mm) |

[Coating Temperature]

A hot-melt adhesive agent was applied to a rubber thread by V-slit coating, and the coated rubber thread was drawn and laid on a nonwoven fabric to obtain coated samples. The coating temperature is the temperature at which the viscosity of a hot-melt adhesive agent becomes 7,000 mPa·s. The open time of a coating applicator was 0.5 seconds, and the coating weight was 0.05 g/m.

A urethane thread (LYCRA (registered trademark)) of 620 detex was used as the rubber thread. The draw ratio of the rubber thread was 2.5 times.

| | |
|---|---|
| A | Coating temperature is lower than 140° C. |
| B | Coating temperature is 140 to 145° C. |
| C | Coating temperature is higher than 145° C. |

[Elasticity Maintenance Ability (Creep Resistance) of Rubber Thread]

In the case of evaluating the coating temperature, samples obtained by laying a rubber thread on a nonwoven fabric were used. Each sample was cut into pieces of 250 mm to 300 mm in length and then laid on a corrugated cardboard sheet in a state of being completely drawn. After marking at any two points so that the rubber length of the specimen becomes 200 mm, using a permanent marker, the rubber was cut at the mark and then left to stand at 40° C. for 1 hour.

After 1 hour, the rubber length was measured and the maintenance rate was calculated. The equation used to calculate the maintenance rate is as follows:

Maintenance rate (%)=rubber length after 1 hour× 100/200

| | |
|---|---|
| A | Maintenance rate is more than 80% |
| B | Maintenance rate is 70 to 80% |
| C | Maintenance rate is less than 70% |

TABLE 4

| | | Example 1 | Example 2 | Example 3 | Example 4 | Example 5 |
|---|---|---|---|---|---|---|
| Viscosity (mPa · s) | 140° C. | 5,788 | 6,888 | 6,975 | 5,175 | 5,638 |
| | | A | B | B | A | A |
| | 160° C. | 2,380 | 2,885 | 2,890 | 2,160 | 2,360 |
| | | A | B | B | A | A |
| Peel strength (g/25 mm) | 20° C. | 2,129 | 2,045 | 2,126 | 2,091 | 2,337 |
| | | A | A | A | A | A |
| Loop tack (g/25 mm) | | 2,262 | 2,023 | 2,525 | 2,091 | 2,174 |
| | | A | A | A | A | A |
| Evaluation of coating | Coating temperature (° C.) | 137 | 140 | 140 | 134 | 136 |
| | | A | B | B | A | A |
| | Rubber thread maintenance (%) (Creep resistance) | 85 | 81 | 93 | 80 | 87 |
| | | A | A | A | B | A |

TABLE 5

|  |  | Comp. Example 1 | Comp. Example 2 | Comp. Example 3 | Comp. Example 4 | Comp. Example 5 |
|---|---|---|---|---|---|---|
| Viscosity (mPa·s) | 140° C. | 3,188 | 2,975 | 5,525 | 10,850 | 11,425 |
|  |  | A | A | A | C | C |
|  | 160° C. | 1,475 | 1,365 | 2,165 | 4,913 | 5,100 |
|  |  | A | A | A | C | C |
| Peel strength (g/25 mm) | 20° C. | 1,409 | 1,677 | 809 | 1,394 | 1,495 |
|  |  | C | B | C | C | C |
| Loop tack (g/25 mm) |  | 2,336 | 2,799 | 1,752 | 1,100 | 1,095 |
|  |  | A | A | B | C | C |
| Evaluation of coating | Coating temperature | 124 | 123 | 137 | 150 | 152 |
|  |  | A | A | A | C | C |
|  | Rubber thread maintenance (%) (creep resistance) | 48 | 64 | 83 | 83 | 82 |
|  |  | C | C | A | A | A |

TABLE 6

|  |  | Comp. Example 6 | Comp. Example 7 | Comp. Example 8 |
|---|---|---|---|---|
| Viscosity (mPa·s) | 140° C. | 4,088 | 5,500 | 11,650 |
|  |  | A | A | C |
|  | 160° C. | 1,770 | 2,205 | 4,638 |
|  |  | A | A | C |
| Peel strength (g/25 mm) | 20° C. | 674 | 893 | 1,759 |
|  |  | C | C | B |
| Loop tack (g/25 mm) |  | 789 | 1,541 | 2,286 |
|  |  | C | B | A |
| Evaluation of coating | Coating temperature | 130 | 136 | 150 |
|  |  | A | A | C |
|  | Rubber thread maintenance (%) (Creep resistance) | 71 | 77 | 92 |
|  |  | B | B | A |

As shown in Tables 1 to 6, the hot-melt adhesive agents of Examples are excellent in melt viscosity, peel strength, loop tack, and elasticity maintenance ability of the rubber thread since they include the component (A1) and component (A2). To the contrary, the hot-melt adhesive agents of Comparative Examples are significantly inferior in any one of the respective performances as compared with the hot-melt adhesive agents of Examples since they do not include either the component (A1) or component (A2).

Inclusion of both (A1) and (A2) enables an improvement in the above-mentioned performances of the hot-melt adhesive agent of the present invention, and a paper diaper including a rubber thread coated with the hot-melt adhesive agent incorporated thereinto is easy to fit the body.

INDUSTRIAL APPLICABILITY

The present invention provides a hot-melt adhesive agent, and a disposable product which is obtained by applying the hot-melt adhesive agent. The hot-melt adhesive agent according to the present invention is particularly suitable for the production of a disposable product.

The invention claimed is:

1. A hot-melt adhesive agent consisting of:
    (A) a mixture of a copolymer of vinyl class aromatic hydrocarbons and conjugated diene compounds consisting of (A1) a three-branched radial styrene-butadiene block copolymer having a styrene content of 35 to 45% by weight and a diblock content of 50 to 90% by weight, and having a viscosity at 25° C. as a 25% (by weight) toluene solution of not more than 250 mPa·s; and (A2) a linear styrene-isoprene block copolymer having a styrene content of less than 30% by weight, and having a viscosity at 25° C. as a 25% (by weight) toluene solution of more than 250 mPa·s;
    (B) a tackifier resin; and
    (C) an optional component selected from the group consisting of a plasticizer, a stabilizer, fine particle fillers, or mixtures thereof
    wherein the viscosity of the hot-melt adhesive agent is less than 5,000 mPa·s, measured with a Brookfield RVT spindle No. 27 at 140° C.,
    wherein the peel strength of the hot melt adhesive agent is greater than 2,000 gf/inch on PET film, and
    wherein the rubber thread maintenance rate of the hot-melt adhesive agent is greater than 80% after one hour.

2. The hot-melt adhesive agent according to claim 1, wherein the tackifier resin is a α-methylstyrene resin.

3. An article comprising the hot-melt adhesive agent according to claim 1.

4. The article of claim 3, which is a disposable product.

5. A hot-melt adhesive agent consisting essentially of:
    (A) a mixture of a copolymer of vinyl class aromatic hydrocarbons and conjugated diene compounds consisting of (A1) a three-branched radial styrene-butadiene block copolymer having a styrene content of 35 to 45% by weight and a diblock content of 50 to 90% by weight, and having a viscosity at 25° C. as a 25% (by weight) toluene solution of not more than 250 mPa·s; and (A2) a linear styrene-isoprene block copolymer having a styrene content of less than 30% by weight, and having a viscosity at 25° C. as a 25% (by weight) toluene solution of more than 250 mPa·s;
    (B) a tackifier resin;
    (C) a plasticizer; and
    (D) a stabilizer
    wherein the viscosity of the hot-melt adhesive agent is less than 5,000 mPa·s, measured with a Brookfield RVT spindle No. 27 at 140° C.,
    wherein the peel strength of the hot melt adhesive agent is greater than 2,000 gf/inch on PET film, and
    wherein the rubber thread maintenance rate of the hot-melt adhesive agent is greater than 80% after one hour.

6. The hot-melt adhesive agent according to claim 5, wherein the tackifier resin is a α-methylstyrene resin.

7. An article comprising the hot-melt adhesive agent according to claim 5.

8. The article of claim 7, which is a disposable product.

* * * * *